US010677707B2

(12) United States Patent
Dusterhoft et al.

(10) Patent No.: US 10,677,707 B2
(45) Date of Patent: Jun. 9, 2020

(54) EVALUATING STRESS-DEPENDENT PERMEABILITY IN UNSTEADY-STATE CONDITIONS AND/OR QUALITY OF MICROPROPPANT PLACEMENT IN SUBTERRANEAN FORMATIONS

(71) Applicant: Halliburton Energy Services, Inc., Houston, TX (US)

(72) Inventors: Ronald Glen Dusterhoft, Katy, TX (US); Vladimir Nikolayevich Martysevich, Spring, TX (US); Brice Kim, Bryan, TX (US); Ibrahim Yucel Akkutlu, College Station, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 266 days.

(21) Appl. No.: 15/879,863

(22) Filed: Jan. 25, 2018

(65) Prior Publication Data

US 2019/0226970 A1 Jul. 25, 2019

(51) Int. Cl.
*E21B 49/00* (2006.01)
*G01N 15/08* (2006.01)
(Continued)

(52) U.S. Cl.
CPC ......... *G01N 15/0826* (2013.01); *E21B 49/00* (2013.01); *G01N 15/08* (2013.01);
(Continued)

(58) Field of Classification Search
CPC .......... E21B 49/00; E21B 49/02; E21B 43/26; E21B 43/267; G01N 15/0826; G01N 15/08; G01N 33/225; G01N 33/28
See application file for complete search history.

(56) References Cited

U.S. PATENT DOCUMENTS 4,710,948 A * 12/1987 Withjack ............... G01N 23/04
378/208
8,920,029 B2 * 12/2014 Maucec ................. G01N 33/24
378/208
(Continued)

OTHER PUBLICATIONS

Wasaki, A., & Akkutlu, I. Y. (Dec. 1, 2015). Permeability of Organic-Rich Shale. Society of Petroleum Engineers. doi:10.2118/170830-PA.

*Primary Examiner* — Daniel P Stephenson
(74) *Attorney, Agent, or Firm* — Thomas Rooney; Baker Botts L.L.P.

(57) ABSTRACT

Systems and methods for evaluating permeability at unsteady-state pressure conditions and areal distribution of microproppants are provided. In some embodiments, the methods comprise: obtaining a first dataset relating to a positive permeability through a split core plug sample of a subterranean formation at a plurality of different differential pressures; obtaining a second dataset relating to a positive permeability through the split core plug sample at each different differential pressure after a plurality of microproppant particles have been placed between two halves of the sample; extrapolating a baseline positive permeability of the sample at a differential pressure equal to zero based on the first dataset; extrapolating a treated positive permeability of the sample at a differential pressure equal to zero based on the second dataset; calculating a closure resistance of the fracture and the fracture closure pressure using the second dataset; and estimating a proppant areal placement factor.

20 Claims, 7 Drawing Sheets

(51) Int. Cl.
*E21B 43/267* (2006.01)
*E21B 43/26* (2006.01)
*E21B 49/02* (2006.01)
*G01N 33/28* (2006.01)
*G01N 33/22* (2006.01)

(52) U.S. Cl.
CPC ............ *E21B 43/26* (2013.01); *E21B 43/267* (2013.01); *E21B 49/02* (2013.01); *G01N 33/225* (2013.01); *G01N 33/28* (2013.01)

(56) References Cited

U.S. PATENT DOCUMENTS

| | | | |
|---|---|---|---|
| 8,985,213 B2 | 3/2015 | Saini et al. | |
| 9,464,523 B1* | 10/2016 | Grove | E21B 49/088 |
| 2010/0258310 A1* | 10/2010 | James | C04B 28/18 |
| | | | 166/277 |
| 2010/0307750 A1* | 12/2010 | Drochon | C09K 8/428 |
| | | | 166/285 |
| 2012/0059590 A1* | 3/2012 | Ameen | G01N 3/58 |
| | | | 702/11 |
| 2016/0053160 A1* | 2/2016 | Nguyen | C09K 8/68 |
| | | | 166/308.5 |
| 2018/0003619 A1* | 1/2018 | Sieben | G01N 21/553 |
| 2018/0163535 A1* | 6/2018 | Quintero | E21B 25/08 |
| 2018/0335374 A1* | 11/2018 | Kanj | G01N 15/0826 |
| 2019/0226970 A1* | 7/2019 | Dusterhoft | E21B 49/00 |

* cited by examiner

EVALUATING STRESS-DEPENDENT PERMEABILITY IN UNSTEADY-STATE CONDITIONS AND/OR QUALITY OF MICROPROPPANT PLACEMENT IN SUBTERRANEAN FORMATIONS

BACKGROUND

The present disclosure relates to certain systems and methods for evaluating permeability and/or microproppant placement in subterranean formations.

In order to efficiently produce hydrocarbons from a subterranean formation, the formation should be sufficiently conductive in order to allow the hydrocarbons to flow to the wellbore. Various treatments for increasing the conductivity of a subterranean formation have been developed, including hydraulic fracturing treatments.

Fracturing tight formations of unconventional reservoirs, such as formations containing shale, tight sandstone formations and coal bed formations, requires special considerations. For example, shale, coal and other types of formations can have a permeability of approximately 1 millidarcy (mD) or less. Hydraulically fracturing such formations typically forms a complex fracture network that includes primary fractures (and branches thereof) and microfractures (including natural microfractures and induced secondary microfractures) in a zone of the formation surrounding the wellbore. For example, the microfractures can extend from a tip and edges of a primary fracture or a branch thereof and extend outwardly in a branching tree-like manner from the primary fracture. The microfractures can extend transversely to the trajectory of the primary fractures allowing them to reach and link natural fracture both in and adjacent to the trajectory of the primary fractures. The microfractures can exist and be formed in both near-wellbore and far-field regions of the zone, as well as regions located adjacent to primary fracture branches. As a result, the microfractures can give more depth and breadth to the fracture network.

In the absence of proppant particulates, the microfractures tend to close back once the hydraulic pressure placed on the formation is released or decreased. Conventional or traditional proppant particulates are often too large to prop the microfractures open. As a result, due to their size, conventional proppant particulates cannot be easily placed in microfractures. Allowing the microfractures to close cuts off a significant portion of the fracture network and ultimately prevents the production of valuable hydrocarbons therefrom.

In order to address this issue, micro-proppant particulates having a size sufficient to allow the particulates to be placed in microfractures have been developed. The microproppant particulates are included in the pad fluid stages of the fracturing treatment. Including microproppant particulates in the pad fluid places the microproppant particulates in the fissure openings to and otherwise in the microfractures as soon as they are opened or created. By holding the microfractures open, the microproppant particulates help maintain fluid communication between the microfractures and the primary fractures. Conventional proppant particulates are then included in the proppant-slurry stages of the fracturing treatment and placed in the primary fractures and branches to help ensure that fluid conductive flow paths to the wellbore are maintained. However, the stimulation of tight formations often involves complex interactions between the formation and the injected fluid-proppant mixture, which may depend on various factors relating to the mechanical properties and/or composition of the formation itself as well as those of the micro-proppants. For example, the deposition of an incomplete monolayer of microproppants in a microfracture may inhibit the conductivity of that microfracture.

SUMMARY OF THE DISCLOSURE

The present disclosure relates to certain systems and methods for evaluating permeability and/or microproppant placement in subterranean formations. More particularly, the present disclosure relates to systems and methods for evaluating permeability at unsteady-state pressure conditions and areal distribution of microproppants.

In some embodiments, the methods of the present disclosure comprise: placing a split core plug sample of a subterranean formation in a pressurizable chamber, the split core plug sample having a first end and a second end opposite the first end; pressurizing the pressurizable chamber to a first differential pressure; releasing pressure from an end of the pressurizable chamber corresponding to the first end of the split core plug sample; obtaining a first pressure change value corresponding to a decrease in pressure measured at an end of the pressurizable chamber corresponding to the second end of the split core plug sample; obtaining a second pressure change value corresponding to an increase in pressure measured at the end of the pressurizable chamber corresponding to the first end of the split core plug sample; and calculating a permeability of the split core plug sample at the first differential pressure using the first pressure change value and the second pressure change value.

In some embodiments, the methods of the present disclosure comprise: obtaining a first set of data that comprises a first plurality of permeability values that each correspond to a positive permeability through a split core plug sample of a subterranean formation at one of a plurality of different differential pressures; obtaining a second set of data that comprises a second plurality of permeability values that each correspond to a positive permeability through the split core plug sample at each of the plurality of different differential pressures after a plurality of microproppant particles have been placed between two halves of the split core plug sample; extrapolating a baseline positive permeability of the split core plug sample at a differential pressure equal to zero ($k_0$) based on the first set of data; extrapolating a treated positive permeability of the split core plug sample at a differential pressure equal to zero ($\kappa$) based on the second set of data; calculating a closure resistance of the fracture (m) and the fracture closure pressure ($p_{seal}$) using the second set of data and $k_0$; estimating a proppant areal placement factor ($\eta_A$) by calculating $k_{model}$ at each of the plurality of different differential pressures for an initial value of $\eta_A$ using:

$$k = \kappa\left[1 - \left(\frac{p_c - \alpha p}{\Pi}\right)^M\right]^3$$

wherein $$\kappa = k_0\left(1 + \frac{0.78 d_p \eta_A}{\sqrt[3]{3\pi D k_0}}\left(\frac{d_p}{\sqrt[3]{3\pi D k_0} + d_p}\right)^{3/2}\right)^3,$$

$$\Pi = \frac{p_{seal}E_p(D + d_p\eta_A)(M/m)}{E_r d_p \eta_A + E_p D}\left(1 + \frac{0.78 d_p \eta_A}{\sqrt[3]{3\pi D k_0}}\left(\frac{d_p}{\sqrt[3]{3\pi D k_0} + d_p}\right)^{3/2}\right), \text{ and}$$

$$M = m(1-\eta_A) + \eta_A\left[m\left(\frac{\sqrt[3]{3\pi D k_0}}{\sqrt[3]{3\pi D k_0} + 0.78 d_p}\right) + \zeta\left(\frac{0.78 d_p}{\sqrt[3]{3\pi D k_0} + 0.78 d_p}\right)\right],$$

and selecting an estimated value of $\eta_A$ that minimizes a total least squares error equal to the sum of each value of $k_{model}$ and each of the second plurality of permeability values.

In some embodiments, the methods of the present disclosure comprise: obtaining a first set of data that comprises a first plurality of permeability values that each correspond to a positive permeability through a split core plug sample of a subterranean formation at one of a plurality of different differential pressures, wherein obtaining at least a portion of the first set of data comprises: placing the split core plug sample in a pressurizable chamber, the split core plug sample having a first end and a second end opposite the first end, pressurizing the pressurizable chamber to a first differential pressure, releasing pressure from an end of the pressurizable chamber corresponding to the first end of the split core plug sample, obtaining a first pressure change value corresponding to a decrease in pressure measured at an end of the pressurizable chamber corresponding to the second end of the split core plug sample, obtaining a second pressure change value corresponding to an increase in pressure measured at the end of the pressurizable chamber corresponding to the first end of the split core plug sample, and calculating a permeability of the split core plug sample at the first differential pressure using the first pressure change value and the second pressure change value; obtaining a second set of data that comprises a second plurality of permeability values that each correspond to a positive permeability through the split core plug sample at each of the plurality of different differential pressures after a plurality of microproppant particles have been placed between two halves of the split core plug sample, wherein obtaining at least a portion of the second set of data comprises: placing the split core plug sample with the plurality of microproppant particles placed between two halves of the split core plug sample in a pressurizable chamber, the split core plug sample having a first end and a second end opposite the first end, pressurizing the pressurizable chamber to a second differential pressure, releasing pressure from an end of the pressurizable chamber corresponding to the first end of the split core plug sample, obtaining a third pressure change value corresponding to a decrease in pressure measured at an end of the pressurizable chamber corresponding to the second end of the split core plug sample, obtaining a fourth pressure change value corresponding to an increase in pressure measured at the end of the pressurizable chamber corresponding to the first end of the split core plug sample, and calculating a permeability of the split core plug sample at the second differential pressure using the third pressure change value and the fourth pressure change value; extrapolating a baseline positive permeability of the split core plug sample at a differential pressure equal to zero ($k_0$) based on the first set of data; extrapolating a treated positive permeability of the split core plug sample at a differential pressure equal to zero ($\kappa$) based on the second set of data; calculating a closure resistance of the fracture (m) and the fracture closure pressure ($p_{seal}$) using the second set of data and $k_0$; estimating a proppant areal placement factor ($\eta_A$) by calculating $k_{model}$ at each of the plurality of different differential pressures for an initial value of $\eta_A$ using:

$$k = \kappa \left[ 1 - \left( \frac{p_c - \alpha p}{\Pi} \right)^M \right]^3$$

wherein $$\kappa = k_0 \left( 1 + \frac{0.78 d_p \eta_A}{\sqrt[3]{3\pi D k_0}} \left( \frac{d_p}{\sqrt[3]{3\pi D k_0} + d_p} \right)^{3/2} \right)^3,$$

$$\Pi = \frac{p_{seal} E_p (D + d_p \eta_A)(M/m)}{E_r d_p \eta_A + E_p D} \left( 1 + \frac{0.78 d_p \eta_A}{\sqrt[3]{3\pi D k_0}} \left( \frac{d_p}{\sqrt[3]{3\pi D k_0} + d_p} \right)^{3/2} \right), \text{ and}$$

$$M = m(1 - \eta_A) + \eta_A \left[ m \left( \frac{\sqrt[3]{3\pi D k_0}}{\sqrt[3]{3\pi D k_0} + 0.78 d_p} \right) + \zeta \left( \frac{0.78 d_p}{\sqrt[3]{3\pi D k_0} + 0.78 d_p} \right) \right],$$

and
selecting an estimated value of $\eta_A$ that minimizes a total least squares error equal to the sum of each value of $k_{model}$ and each of the second plurality of permeability values.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present disclosure, and should not be used to limit or define the claims.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

The present disclosure relates to certain systems and methods for evaluating permeability and/or microproppant placement in subterranean formations. More particularly, the present disclosure relates to systems and methods for evaluating permeability at unsteady-state pressure conditions and areal distribution of microproppants.

The present disclosure provides methods and systems for evaluating permeability at unsteady-state pressure conditions and areal distribution of microproppants using split core plug samples with microproppants that includes measuring the effect of the stimulation as a change in permeability of the sample under confining stress. As used herein, the term "unsteady-state" or variations thereof refers to a condition or property (e.g., pressure, temperature, stress, etc.) that is not a constant in the system during the relevant time period. However, this term is not intended to require any particular degree of instability in such a system. The proposed laboratory method includes two stages: measurement before the stimulation of the cores and measurements after the stimulation. The first stage measurements involve measuring the permeability of the split core plug under changing stress conditions to identify the base conditions that are necessary after the stimulation in quantifying the degree of stimulation. In the second stage, each sample is treated with a microproppant slurry, and the treated sample permeability is measured again under changing stress. In the methods of the present disclosure, the pressure pulse decay method is used for the measurements and an analytical permeability model is introduced to calculate permeability at unsteady-state pressure conditions. Parameter $\eta_A$ of the permeability model is introduced as the areal monolayer proppant placement quality factor. In one aspect of the present disclosure, methods and systems for measuring permeability of a split core plug at unsteady-state pressure conditions are provided. In another aspect of the present disclosure, methods and systems are provided that use a mechanistic analytical permeability model to analyze the quality of microproppant placement in the fracture (e.g., the areal monolayer proppant placement quality factor) in the stimulated core samples.

Among the many potential advantages to the methods and compositions of the present disclosure, only some of which are alluded to herein, the methods, compositions, and systems of the present disclosure may evaluate the permeability of a formation sample more accurately, for example, with regard to several factors that affect permeability, including fracture face interactions, confining pressure, and the like. In some embodiments, the equalization of pressure across the core sample as discussed below, may more accurately simulate fluid flow or permeability through the entirety of the formation sample, not just through a crack or microfracture between the halves of the split core sample. In some embodiments, the methods of the present disclosure also may better predict the effectiveness of microproppant treatments and/or other fracture permeability treatments, among other reasons, by quantifying the areal distribution of microproppants in a fracture.

As noted above, one aspect of the present disclosure provides method and systems for performing permeability measurements at unsteady-state pressure conditions on a split core plug sample. The split core plug samples used in the methods and systems of the present disclosure may be prepared using any suitable method. For example, the core plugs may be cut perpendicular to the axis of the core sample or parallel to the axis (e.g., called horizontal and vertical plugs, respectively) when cut from a vertical wellbore. The terms horizontal and vertical may be applied for cores cut from a deviated or horizontal wellbore, even though they are not strictly correct unless core orientation is measured and plugs are cut to the true in-situ orientation. In some embodiments, the core plugs may be about 1 to 1.5 inches (2.5 to 3.8 cm) in diameter and 1 to 2 inches (2.5 to 5 cm) long, although in other embodiments the core plugs may be of any suitable size and/or dimensions. The core plugs may be split by any suitable means, such as mechanical and/or hydraulic cracking or by cutting with a saw. In some embodiments, cracking methods may create fractures that more accurately mimic natural fractures and/or may exactly match the shapes of both fracture faces. Conversely, cutting techniques can provide a more simple geometry. In some embodiments, split core plug samples may be created by cutting the core plugs along the axis of a generally cylindrical plug using a thin (e.g., about 0.4 mm) diamond blade circular saw, either with or without cooling fluids. After cutting, the parts of the core plug may put together and placed into the testing apparatus for the stimulation. In some embodiments, the parts of the core plug may be used in the same chamber without enforcing or holding them together.

Figure 1:
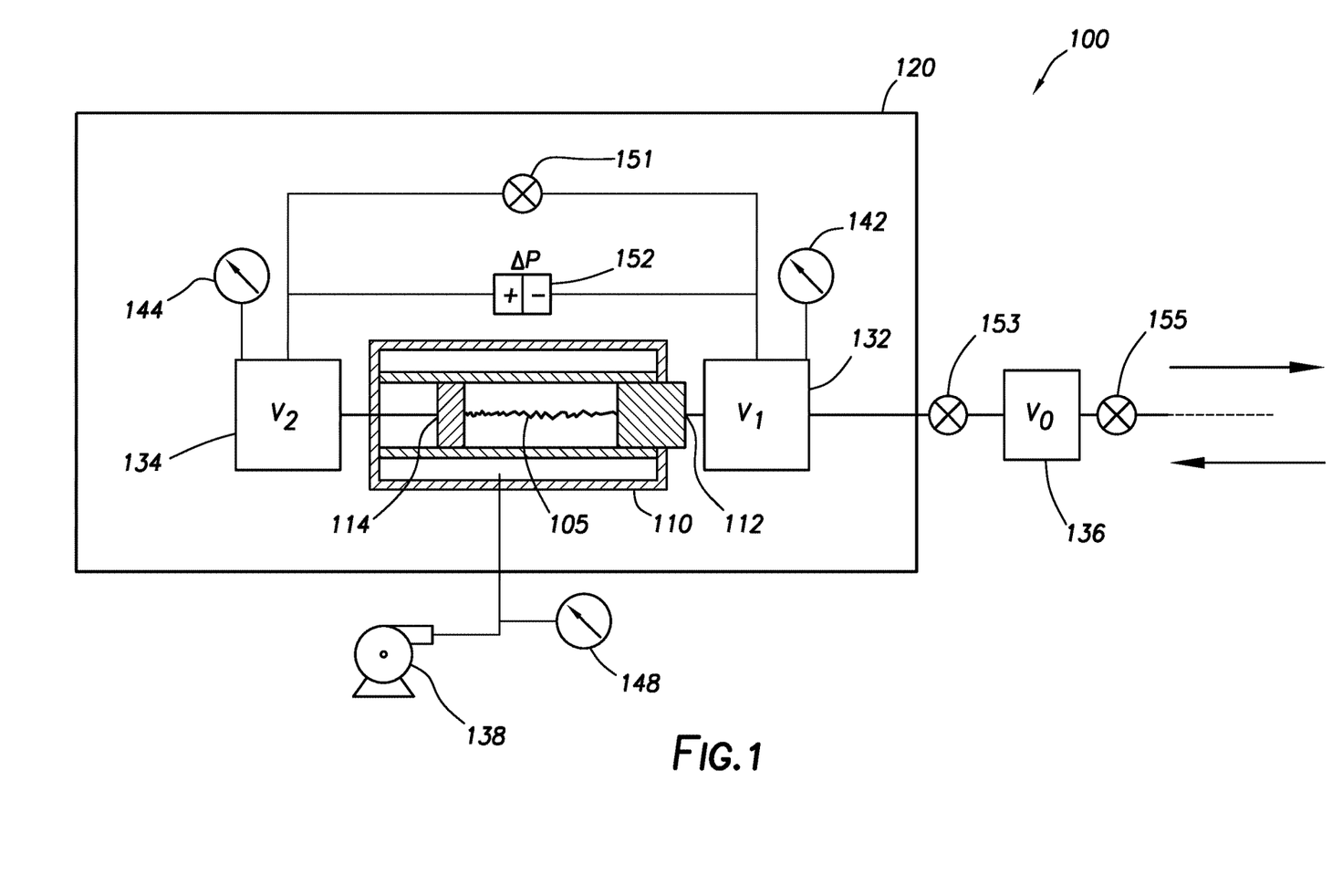
FIG. 1 is a diagram illustrating an apparatus for performing permeability measurements at unsteady-state pressure conditions according to certain embodiments of the present disclosure.

An example of a laboratory apparatus for performing permeability measurements at unsteady-state pressure conditions according to certain embodiments of the present disclosure is depicted in FIG. 1. The testing apparatus 100 includes a hydrostatic cylinder vessel 110 placed inside of a temperature-controlled chamber 120, which allows the measurements to be performed under isothermal conditions. Temperature-controlled chamber 120 also may be equipped with heating elements, cooling elements, or other cooling/heating devices (not shown) that may be used to increase or decrease the temperature within temperature-controlled chamber 120. The hydrostatic cylinder vessel 110 includes an inlet 112 at one end and an outlet 114 at the opposite end, that are each in fluid communication with one of fixed-volume chambers 132 and 134. In other embodiments, the apparatus may be equipped with only one fixed-volume chamber, or no fixed volume chamber at all. The pressure values at the inlet and outlet of the cylinder vessel may be monitored using pressure sensors 142 and 144. Fixed-volume chambers 132 and 134 also may be in fluid communication with each other, which may be controlled using valve 151 (e.g., valve 151 may be closed during testing, or opened to allow pressure between the chambers 132 and 134 to equalize). A differential pressure sensor 152 (e.g., a differential pressure transducer) may be used to measure the pressure difference between chambers 132 and 134. Pressure sensors 142 and 144 and differential pressure sensor 152 may comprise any sensor devices suitable for measuring pressure (e.g., pressure transducers), which may utilize an analog-to-digital converter and/or interface with a computer device. Chamber 132 also may be in fluid communication with another fixed-volume chamber 136, and flow between chambers 132 and 136 may be regulated by valve 153.

Initially, the split core plug sample 105 is placed in a core holder inside the cylinder vessel 110 and confined to a high pressure, which simulates fracture closure stress. Next, all valves are opened to gradually pressurize the sample with a measurement fluid. Any suitable measurement fluid for applying pressure to the hydrostatic cylinder vessel 110 may be used, such as nitrogen. After reaching equilibrium, when the pressure is stabilized in the system, a confining pressure is created in the hydrostatic cylinder vessel 110 using a pump 138. Any suitable laboratory or testing pump may be used, such as a laboratory syringe pump. The differential pressure (e.g., a pressure difference between the confinement pressure and the pore pressure) created by pump 138 may be monitored by pressure sensor 148. In some embodiments, the differential pressure may be equal to or greater than 300 pounds per square inch (psi). In some embodiments, the differential pressure is maintained above 1,000 psi, among other reasons, to minimize the Klinkenberg slippage effect. In some embodiments, the pressure difference between inlet 112 and outlet 114 is maintained at a high enough level to eliminate a molecular diffusion effect within vessel 110.

Next, a pressure pulse is created by adjusting the pressure at chamber 136, by either charging or discharging the volume. This process causes a pressure differential when the valve 153 between the chambers 136 and 132 is opened. A sudden change in the downstream pressure gives the effect of a pulse across the nitrogen-saturated sample, and this pulse leads to the transport of nitrogen through the sample from the high-pressure end to the low-pressure end. During the transport, the sample experiences a pressure transient such that the inlet pressure decays and the outlet pressure builds up. The transport continues until the two pressures reach a stabilized final pressure value. The pressure vs. time data may be recorded for the subsequent analysis and permeability estimation.

Flow into or out of fixed-volume chamber 136 (and out of the overall system 100) may be regulated by valve 155. In some embodiments, one or more of valves 151, 153, or 155, pump 138, and/or heating or cooling elements associated with temperature-controlled chamber 120 may be controlled by an information handling system such as a computer processing device. In some embodiments, such a computer device also may be communicatively coupled to and receive data from one or more of pressure sensors 142, 144, and/or 148.

Figure 2A:
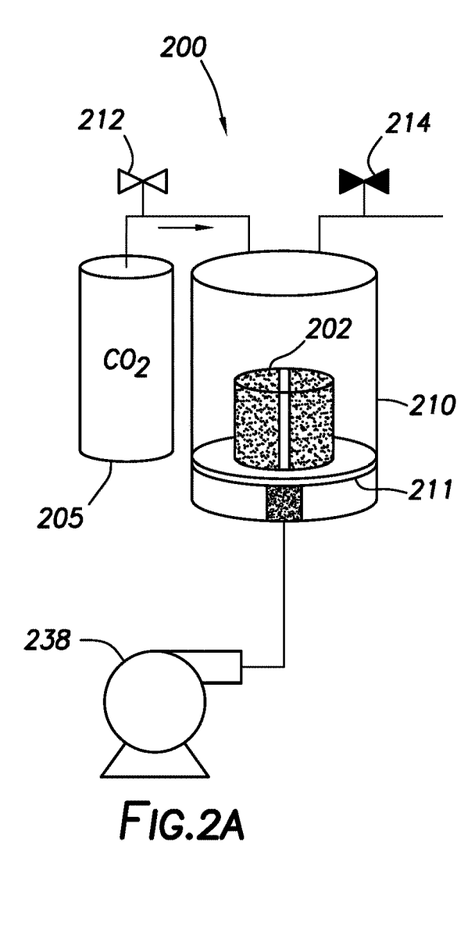
FIGS. 2A, 2B, and 2C are diagrams illustrating an apparatus for testing stimulation methods on split core plug samples according certain embodiments of the present disclosure.
Figure 2B:
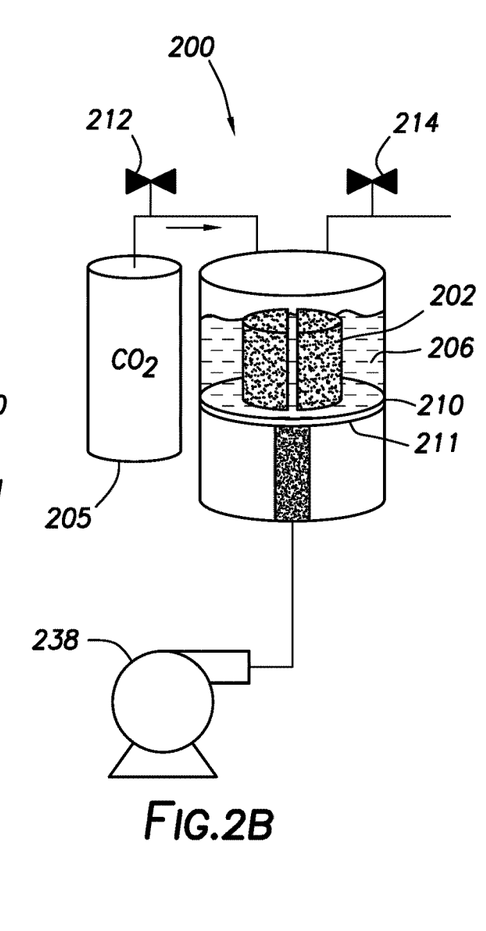
Figure 2C:
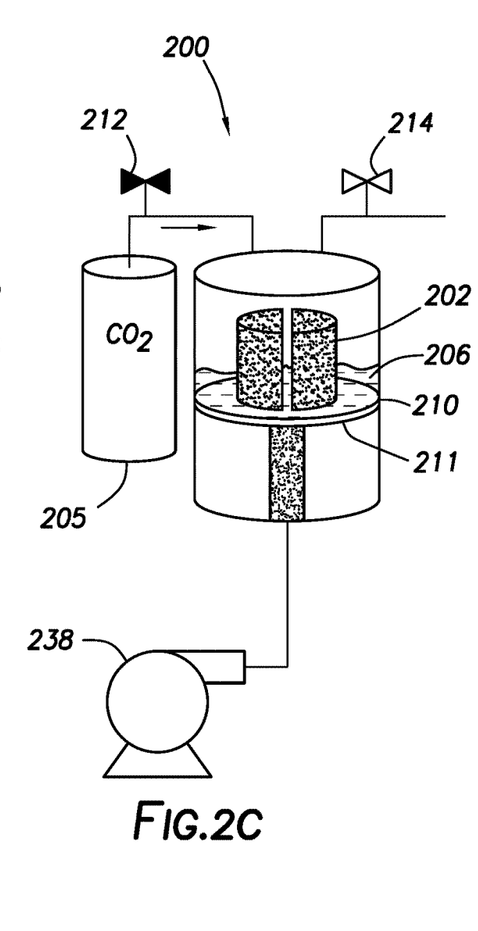

An example of a laboratory apparatus for stimulation or treatment of split core plug samples according to the present disclosure is depicted in FIG. 2. System 200 includes accumulator 210 (in which the split core plug 202 is placed), pump 238, and valves 212 and 214 that control flow into and out of the accumulator. The interior of the accumulator 210 is pressurized using a carrier fluid from tank 205 by opening valve 212. The carrier fluid is used to carry the microproppant particles between the halves of the split core plug 202. Accumulator 210 is equipped with a moving piston 211 that enables the adjustment of its volume.

In the embodiment shown, gaseous phase carbon dioxide is used to pressurize the interior of accumulator 210. However, any liquid or gas may be used, in particular, liquids or gases suitable for carrying microproppants into a fracture. Examples of gases that may be suitable include, but are not limited to nitrogen, air, methane, helium, argon, and any combination thereof. In some embodiments, water may be a less suitable fluid for use as the microproppant-carrying fluid for at least two reasons. First, the shale cores used are often highly interactive with water. Second, using carbon dioxide has the benefit of injecting at high-pressure as liquid into the sample and, after the stimulation, it can be heated and removed as a supercritical fluid from the sample. In some embodiments, the supercritical carbon dioxide may not experience sharp liquid/gas phase change with the changes in pressure; consequently, it may help to avoid developing surface tension forces that may lead to damaging the cores.

Referring back to FIG. 2, initially, in FIG. 2A, the halves of the split core plug 202 are placed into accumulator 210 standing free above the piston 211. At this stage, valve 214 is closed. To convert gaseous carbon dioxide inside the accumulator 210 into liquid phase, with both valves 212 and 214 now closed (as shown in FIG. 2B), the piston 211 is forced by means of a laboratory syringe pump 238 to pressurize the accumulator. According to Boyle's law, when the volume of the accumulator 210 is reduced, the fluid pressure increases. If enough force is applied with the piston 211, the pressurization will convert carbon dioxide into a liquid phase 206 after sufficient time. The process of gas injection and pressurization using the piston 211 is repeated until the liquid buildup in the accumulator is sufficient for the split core 202 to be fully immersed in liquid carbon dioxide 206. At this stage, the liquid carbon dioxide in the accumulator 210 will apply hydrostatic pressure to the split core parts 202. This applied hydrostatic pressure creates a stress field in the rock and leads to the stimulation; the stimulation is defined as any significant improvement of the rock permeability as a result of crack development and/or proppant placement. Fine-scale effects of the liquid carbon dioxide can develop, which change to the microstructure of the rock and may dissolve some soluble organic matter. These effects are not part of the analysis presented in this study and require a detailed investigation. Typically, approximately 6 hours is sufficient to ensure that the stimulation occurs.

At the final stage, the accumulator 210 is heated to a temperature greater than 87.9° F. (31.1° C.), the cricondentherm of carbon dioxide. Sufficient time is given for the fluid to reach the supercritical state. Next, valve 214 is opened, and carbon dioxide is gradually released from the accumulator 210 (as shown in FIG. 2C). During the release, the pressure in the accumulator 210 is reduced, and the supercritical carbon dioxide inside the split core 202 is converted back into the gaseous phase. After the stimulation stage is complete, the accumulator 210 is cooled to ambient conditions, the two pieces of the stimulated core sample 202 are removed from the accumulator 210, and the pieces are re-assembled and placed inside the core holder setup shown in FIG. 1 for the permeability measurements at multiple different confining pressures. These measured permeability values make up the baseline values.

Next, the treatment process described in the previous paragraphs is repeated including carbon dioxide/microproppant slurry, again at multiple different confining pressures. The microproppants are now placed inside the accumulator 210 with the split core sample 202 and pressurized. The same pressure and temperature values are applied during the treatment. The hydrostatic pressure applied with liquid carbon dioxide now forces the microproppants to the outer surfaces of the sample and enables them to penetrate into the matrix and between the halves of the split core plug. If the stimulation stage with microproppants is completed successfully, the sample should show an improvement in its permeability.

Figure 3:
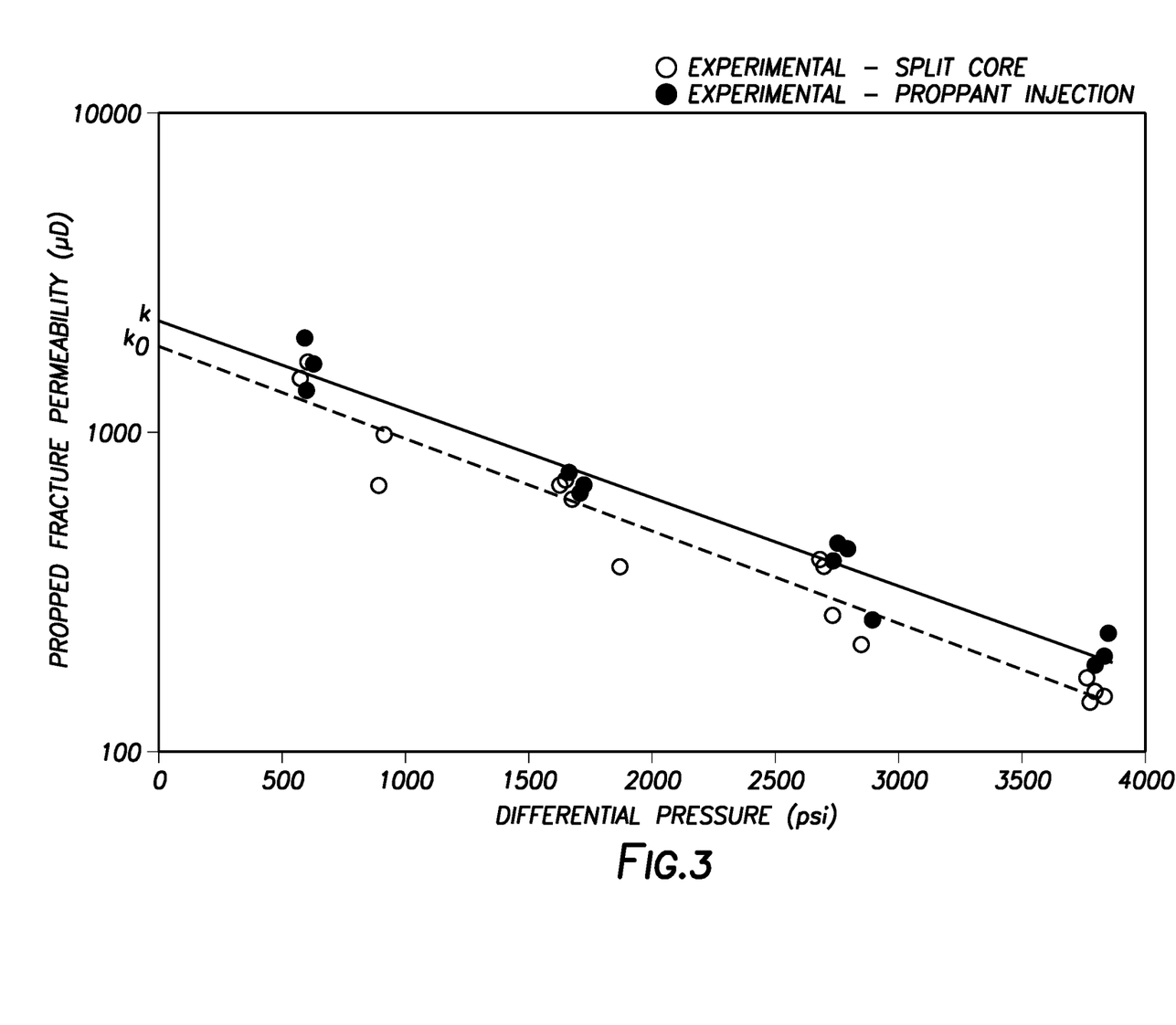
FIG. 3 is a graph of permeability data and best fit lines from testing of a split core plug sample before and after treatment with microproppant according to certain embodiments of the present disclosure.

FIG. 3 is an example of a graph plotting permeability data from tests of a split core plug tested using a method and apparatus as described above. The black dots/line show the data and best fit line for permeability measurements prior to proppant placement, and the red dots/line show the data and best fit line for permeability measurements after proppant placement in the split core plug. The effect of stimulation and proppant placement on permeability is a function of several quantities including the proppant placement quality. That proppant placement quality can be quantified and estimated by comparing the experimental results before and after proppant placement.

As disclosed herein, a propped fracture permeability simulation model that considers the presence of microproppants in the fractures may be used to evaluate the permeability of a split core plug sample treated with such microproppants. One aspect of this model is that it considers the fracture wall-proppant interactions and introduces a new set of parameters, some of which show sensitivity to the propped fracture permeability, the fracture closure stress, and the fracture wall asperity. In the model, these contributions are denoted using three parameters: κ, Π, and M, respectively. When the proppants are uniformly distributed inside the fracture, they affect the permeable paths in the fracture and the closure resistance of the fracture. In addition, fracture wall asperity plays a role in the presence of microproppants. The quality of the proppant injection and distribution inside the fracture are introduced. The latter requires using the proppant areal placement factor, $\eta_A$, the proppant height effectiveness factor, $\eta_H$, and, finally, the proppant shape factor, ζ: The resulting formulation of the propped fracture permeability, k, is given as a power-law expression according to Equation (1) below:

$$k = \kappa \left[ 1 - \left( \frac{p_c - \alpha p_p}{\Pi} \right)^M \right]^3 \quad (1)$$

where $p_c - \alpha p_p$ is the effective stress applied to the core plug. Each of κ, Π, and M can be expressed according to Equations (2), (3), and (4), respectively.

$$\kappa = k_0 \left( 1 + \frac{0.78 d_p \eta_A}{\sqrt[3]{3\pi D k_0}} \left( \frac{d_p}{\sqrt[3]{3\pi D k_0} + d_p} \right)^{3/2} \right)^3 \quad (2)$$

$$\Pi = \frac{p_{seal} E_p (D + d_p \eta_A)(M/m)}{E_r d_p \eta_A + E_p D} \left( 1 + \frac{0.78 d_p \eta_A}{\sqrt[3]{3\pi D k_0}} \left( \frac{d_p}{\sqrt[3]{3\pi D k_0} + d_p} \right)^{3/2} \right) \quad (3)$$

$$M = m(1 - \eta_A) + \eta_A \left[ m \left( \frac{\sqrt[3]{3\pi D k_0}}{\sqrt[3]{3\pi D k_0} + 0.78 d_p} \right) + \zeta \left( \frac{0.78 d_p}{\sqrt[3]{3\pi D k_0} + 0.78 d_p} \right) \right] \quad (4)$$

where $d_p$ is the diameter of the spherical microproppants, $k_0$ is the permeability of the fracture at zero differential pressure, $p_{seal}$ is the stress to close the fracture completely when $d_p \to 0$, in is the resistance of the fracture to fully close in $d_p \to 0$ limit, D is the diameter of the core plug, ζ is the shape factor of the proppants (ζ=0.364 for spherical microproppants), and $E_r$ and $E_p$ are the Young's moduli of the fracture walls and the proppants, respectively.

Figure 4:
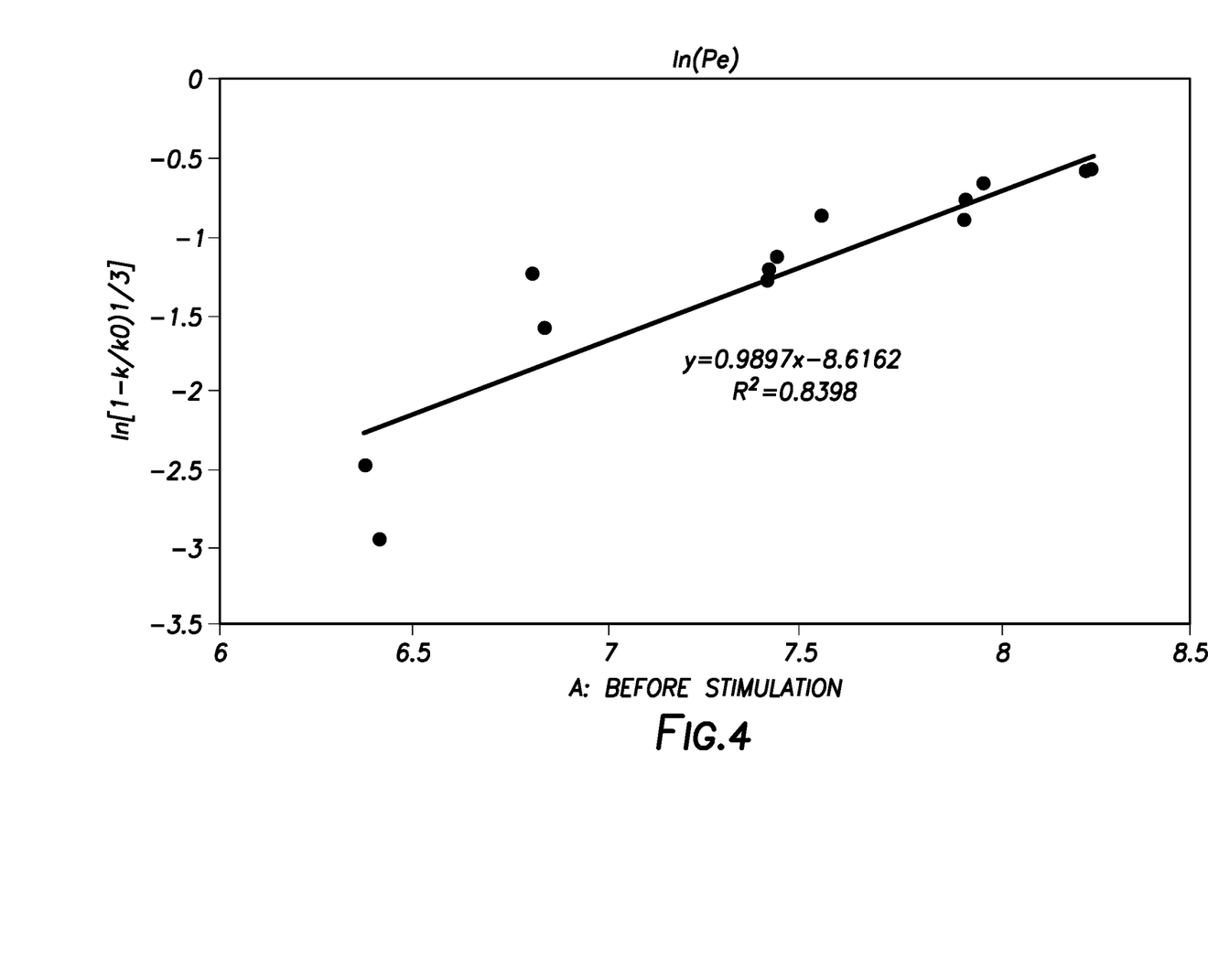
FIG. 4 is a graph of data and best fit lines from testing of a split core plug sample for calculating fracture closure resistance (m) and fracture closure stress ($p_{seal}$) according to certain embodiments of the present disclosure.

The permeability of the fracture at zero differential pressure both before and after proppant placement ($k_0$ and κ, respectively) can be calculated from the measured permeabilities of the fracture as a function of differential pressure at different confining pressures, and extrapolating that data to a confining pressure equal to zero (i.e., the y-intercepts of the best fit lines shown in FIG. 3). The fracture closure stress, $p_{seal}$, and the resistance of the fracture to fully close, m, can be obtained by using the calculated value of $k_0$ and the measured values of k and plotting the natural logarithm of $[1-(k/k_0)^{1/3}]$ as a function of the natural logarithm of the differential pressure, and extrapolating a best fit line. The slope of that best fit line is equal to m, and the y-intercept of that line is equal to $-m \ln(p_{seal})$. An example of such a plot is shown in FIG. 4.

The value of $\eta_A$ for a particular treated sample may be characterized using a least square error method in which a reasonable value of $\eta_A$ is considered as an initial estimate. This initial estimate of $\eta_A$ may depend on a number of factors that will be recognized by a person of skill in the art with the benefit of this disclosure, including but not limited to: the nature, composition, chemistry, or other properties of the fluid used to carry the microproppant into the fracture (e.g., whether the carrier fluid is a liquid, gas, emulsion, dispersion, etc.); the pumping schedule and/or rate at which the fluid is pumped into the fracture; the amount of microproppant in the fluid; the nature, composition, particle size size, and/or amount of the microproppant used; etc.

The error for the value of $\eta_A$ that satisfies Equation (1) is estimated using Equation (5) below:

$$\sum_{i=1}^{n} (k_{Experiment,i} - k_{Model,i})^2 = \text{Least Squares Error} \quad (5)$$

Here, index i represents the number of experimental data points (e.g., the various differential pressures at which permeability was measured). The accuracy of the estimated value of $\eta_A$ may be tested by calculating the difference between the experimentally measured proppant stimulated permeability $k_{Experiment,i}$ (shown in red in FIG. 3) and the calculated measured proppant stimulated permeability $k_{Model,i}$ using the estimated value of $\eta_A$ in an expanded version of Equation (1) in which Equations (2), (3), and (4) are substituted into Equation (1) and using the values for in, $k_0$ and $p_{seal}$ calculated as described above. Thus, the value of ηA may be characterized by the following steps: (a) using Equation (1) to calculate $k_{Model,i}$ for the same differential pressure values used in the experimental permeability testing; (b) using Equation (5) to determine the sum of least squares error between $k_{Experiment,i}$ and $k_{Model,i}$; and (c) using a solver to determine an optimum value of $\eta_A$ that yields the minimum least squares error.

The methods and systems of the present disclosure may be used to study the effect of various treatments in subterranean formations such as tight, low permeability formations, including but not limited to shale formations. For example, the data obtained using the methods and systems of the present disclosure may be used in reservoir simulators that are used to design treatments (e.g., hydraulic fracturing treatments, microproppant injection treatments, surfactant treatments, fracture face treatments, etc.) for such formations. In some embodiments, such simulations may be performed prior to a hydraulic fracturing treatment, e.g., in which one or more fracturing fluids are introduced into a subterranean formation (e.g., using one or more pumps) at or above a pressure sufficient to create or enhance one or more fractures in the formation. In other embodiments, such simulations may be performed on formations already fractured but not treated, among other reasons, to determine if the formation would benefit from a microproppant injection treatment, or in evaluating the potential effectiveness of several different possible microproppant injection treatments.

The treatment fluids used in the methods and systems of the present disclosure may comprise any base fluid known in the art, including aqueous base fluids, non-aqueous base fluids, gases, and any combinations thereof. The term "base fluid" refers to the major component of the fluid (as opposed to components dissolved and/or suspended therein), and does not indicate any particular condition or property of that fluids such as its mass, amount, pH, etc. Aqueous fluids that may be suitable for use in the methods and systems of the present disclosure may comprise water from any source. Such aqueous fluids may comprise fresh water, salt water (e.g., water containing one or more salts dissolved therein), brine (e.g., saturated salt water), seawater, or any combination thereof. In most embodiments of the present disclosure, the aqueous fluids comprise one or more ionic species, such as those formed by salts dissolved in water. For example, seawater and/or produced water may comprise a variety of divalent cationic species dissolved therein. In certain embodiments, the density of the aqueous fluid can be adjusted, among other purposes, to provide additional particulate transport and suspension in the compositions of the present disclosure. In certain embodiments, the pH of the aqueous fluid may be adjusted (e.g., by a buffer or other pH adjusting agent) to a specific level, which may depend on, among other factors, the types of viscosifying agents, acids, and other additives included in the fluid. One of ordinary skill in the art, with the benefit of this disclosure, will recognize when such density and/or pH adjustments are appropriate. Examples of non-aqueous fluids that may be suitable for use in the methods and systems of the present disclosure include, but are not limited to, oils, hydrocarbons, organic liquids, and the like. Examples of gases suitable for use in conjunction with the pad fracturing fluid and proppant slurry include, but are not limited to, nitrogen, carbon dioxide, air, methane, helium, argon, and any combination thereof. In certain embodiments, the fracturing fluids may comprise a mixture of one or more fluids and/or gases, including but not limited to emulsions, foams, and the like.

As used herein and in the appended claims, the term "microproppant particulates" or derivations thereof means particulates having a D50 particulate size distribution no greater than 30 microns. For example, the microproppant particulates can have a D50 particulate size distribution in the range of from about 0.01 microns to about 30 microns or any subset therebetween. For example, the microproppant particulates can have a D50 particulate size distribution in the range of from about 1 micron to about 25 microns. For example, the microproppant particulates can have a D50 particulate size distribution in the range of from about 5 microns to about 20 microns. As used herein and in the appended claims, a "D50 particle size distribution" means the value of the particle diameter at 50% in the cumulative distribution. For example, the D50 particle size distribution of the microproppant particulates mixed with the pad fracturing fluid can be greater than the D50 particle size distribution of the microproppant particulates mixed with the proppant slurry. Apart from the above definition of microproppant particulates, the modifier "micro" should not be construed as limiting.

The microproppant particulates used in the methods and systems of the present disclosure may comprise any suitable material. For example, the microproppant particulates may be made of a material selected from the group consisting of silica flour, glass beads, fly ash, ceramics, bauxite, polymer materials, polymeric composites, mica, and any combination thereof. In some embodiments, the microproppant particulates may comprise one or more materials selected from the group consisting of silica flour, fly ash, ceramics, polymeric composites, and combinations thereof. For example, In some embodiments, the microproppant particulates may comprise one or more materials selected from the group consisting of fly ash, ceramics, polymeric composites and combinations thereof. Examples of commercially available micro-proppant particulates that can be used in the disclosed method include micro-proppant particulates manufactured by Zeeospheres Ceramics, LLC and sold as "Zeeospheres N-200" and "Zeeospheres N-600." In some embodiments, the material for the microproppant particulates may be selected for ease of imaging, e.g., with laboratory microscopic equipment. For example, tungsten powder may be used as the microproppant in certain embodiments, among other reasons, because they may emit a bright light during certain forms of scanning and thus may be readily seen in microscopic imaging of a split core plug treated with such microproppant materials.

In certain embodiments, the treatment fluids used in the methods and systems of the present disclosure optionally may comprise any number of additional additives. Examples of such additional additives include, but are not limited to, salts, surfactants, acids, proppant particulates, diverting agents, fluid loss control additives, gas, nitrogen, carbon dioxide, surface modifying agents, tackifying agents, foamers, corrosion inhibitors, scale inhibitors, catalysts, clay control agents, biocides, friction reducers, antifoam agents, bridging agents, flocculants, additional $H_2S$ scavengers, $CO_2$ scavengers, oxygen scavengers, lubricants, additional viscosifiers, breakers, weighting agents, relative permeability modifiers, resins, wetting agents, coating enhancement agents, filter cake removal agents, antifreeze agents (e.g., ethylene glycol), and the like. In certain embodiments, one or more of these additional additives (e.g., a crosslinking agent) may be added to the treatment fluid and/or activated after the viscosifying agent has been at least partially hydrated in the fluid. A person skilled in the art, with the benefit of this disclosure, will recognize the types of additives that may be included in the fluids of the present disclosure for a particular application.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLES

Example 1

Split core plugs were prepared as described above from core samples taken from a Bakken shale formation and a Barnett shale formation. Each of the split core plugs was created by cutting the core plug along its axis using a 0.4 mm diamond blade circular saw without cooling fluids. The permeabilities of each of the core plugs were measured at multiple different confining pressures using apparatus as shown in FIGS. 1 and 2 at three different times: (1) after the core plugs were split, (2) after the split core plugs were treated with carbon dioxide, and (3) after the split core plugs were treated with a carbon dioxide/microproppant slurry. The temperature in the temperature controlled chamber was set to reservoir temperature of 176° F. (80° C.) during the measurements. The measured permeabilities are plotted in FIGS. 5A (Bakken shale) and 5B (Barnett shale).

Figure 5A:
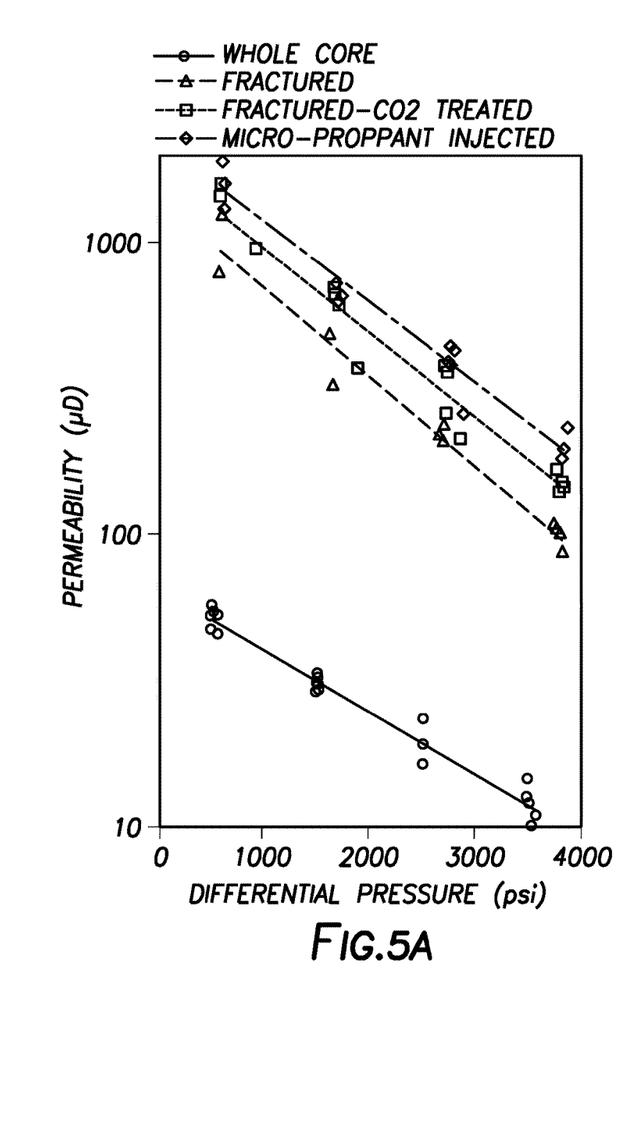
FIGS. 5A and 5B are graphs of permeability data and best fit lines from testing of core plug samples from different formations before and after treatment with microproppant according to certain embodiments of the present disclosure.
Figure 5B:
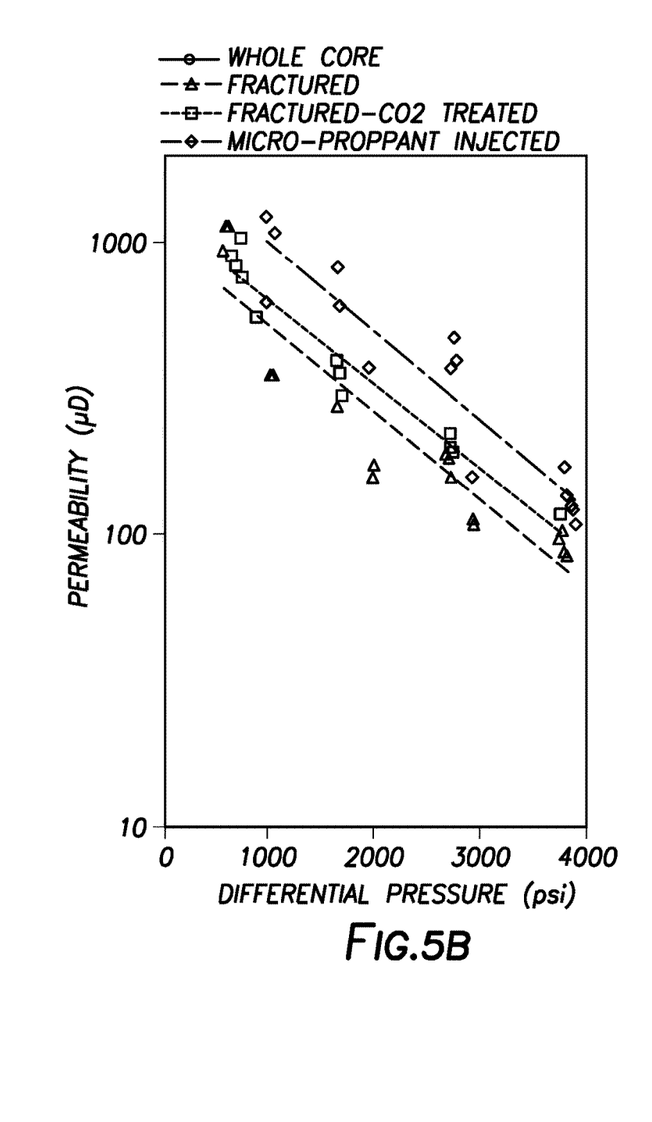

A major portion of the permeability change develops at low differential pressure, when the pore pressure is comparable to that of the confining pressure. As the differential pressure is increased, the fractures close, and permeability is significantly reduced. The sample permeability was predicted to decrease by a factor of 6 as the pressure differential is increased by a factor of 7, from 500 to 3,600 psi. The trend is similar, but the permeability values are much lower, typically changing in the order of 100 nD to 1 μDarcy. Therefore, these results are below the y-axis scale used and are not shown here. FIGS. 5A and 5B show that the stimulation of the split core plugs with liquid $CO_2$ (shown as squares) leads to an improvement in permeability. Further, the subsequent stimulation of the core plugs with the liquid $CO_2$-proppant slurry (shown as diamonds) provides an improvement in addition to the improvement attained by using $CO_2$ only.

Example 2

A series of experiments are conducted with three different downhole shale samples (Bakken, Eagle Ford and Barnett) and one Barnett outcrop sample under varying stress. For each sample, the permeabilities of each of the core plugs were measured at multiple different confining pressures using apparatus as shown in FIGS. 1 and 2 both before and after the split core plugs were treated with microproppant. The Bakken, Eagle Ford, and Barnett shale samples were treated with a carbon dioxide/microproppant slurry according to the method described above. The Barnett outcrop sample was manually propped to exaggerate the proppant distribution in the fracture. For this sample, 0.14 grams of microproppants were manually spread uniformly between the fracture faces, which should give the effects of a substantially complete mono-layer of microproppants.

Figure 6A:
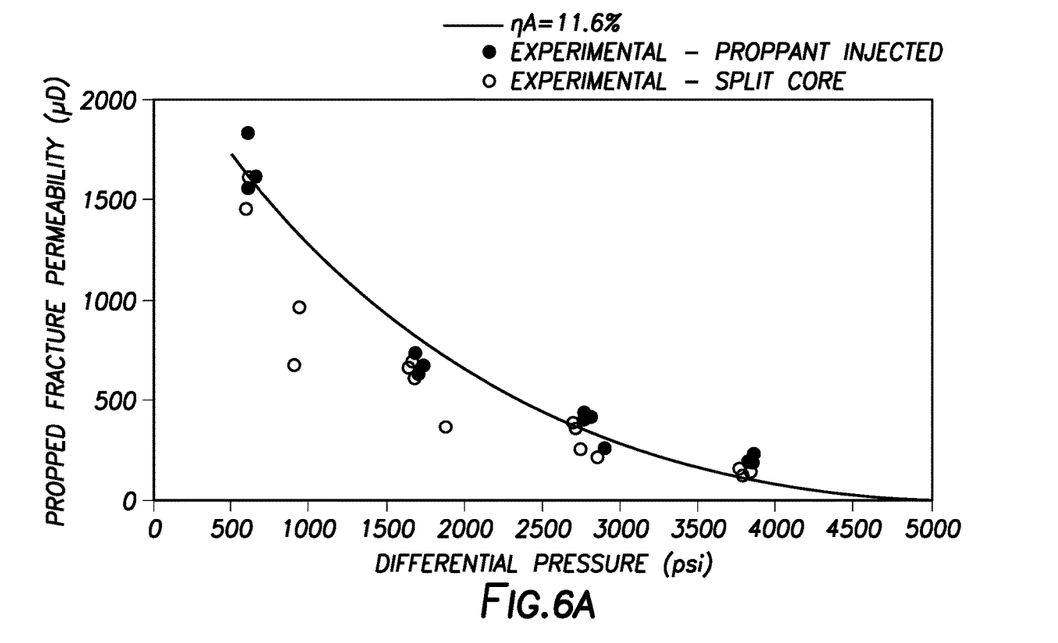
FIGS. 6A, 6B, 6C, and 6D are graphs of experimental and modeled permeability data for split core plug samples from different formations according to certain embodiments of the present disclosure.
Figure 6B:
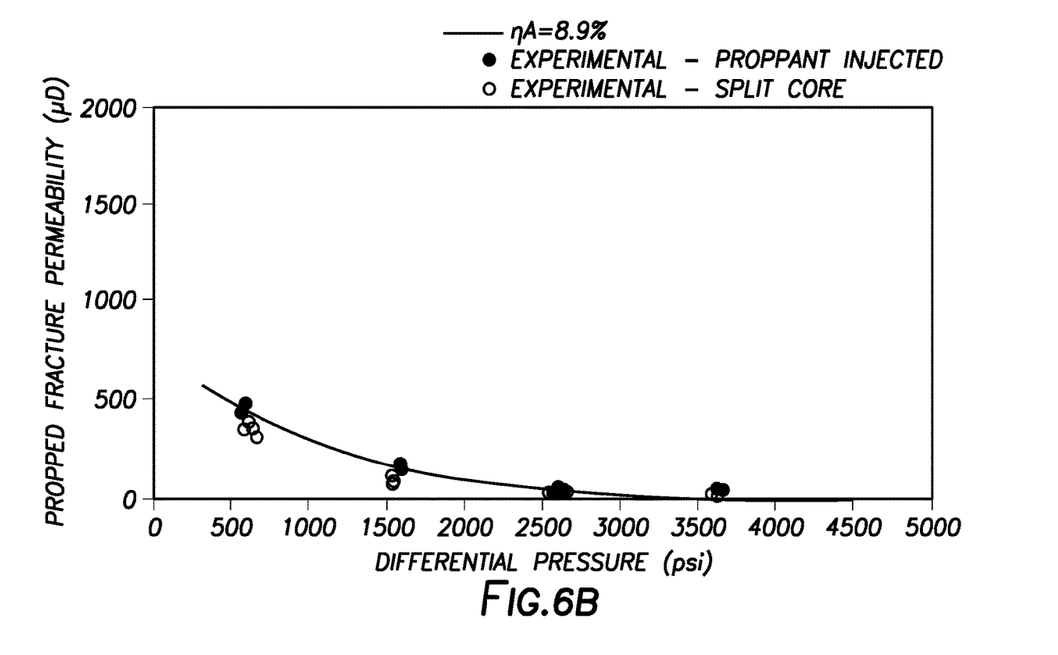
Figure 6C:
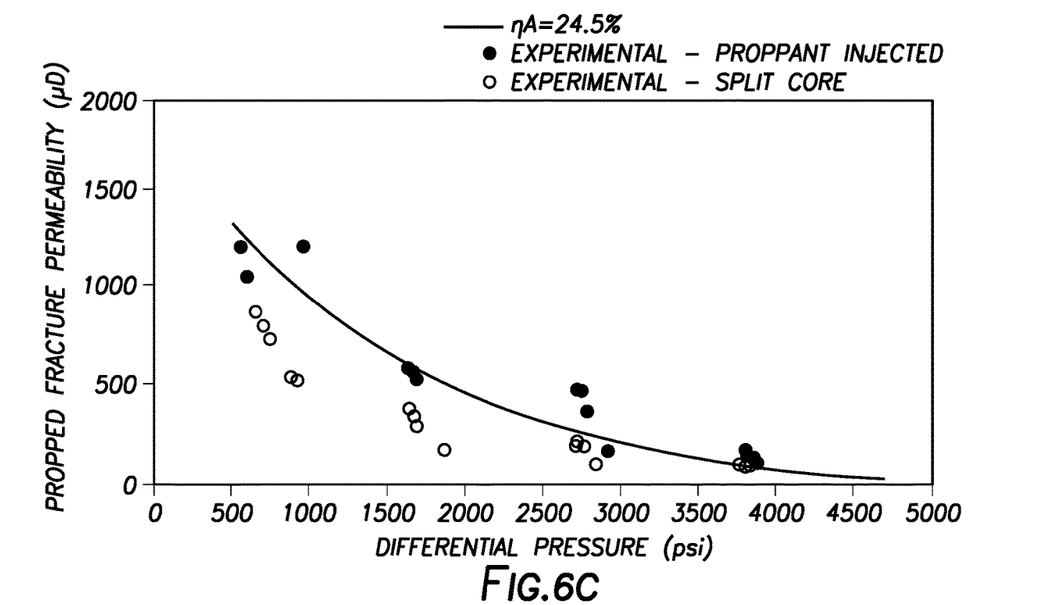
Figure 6D:
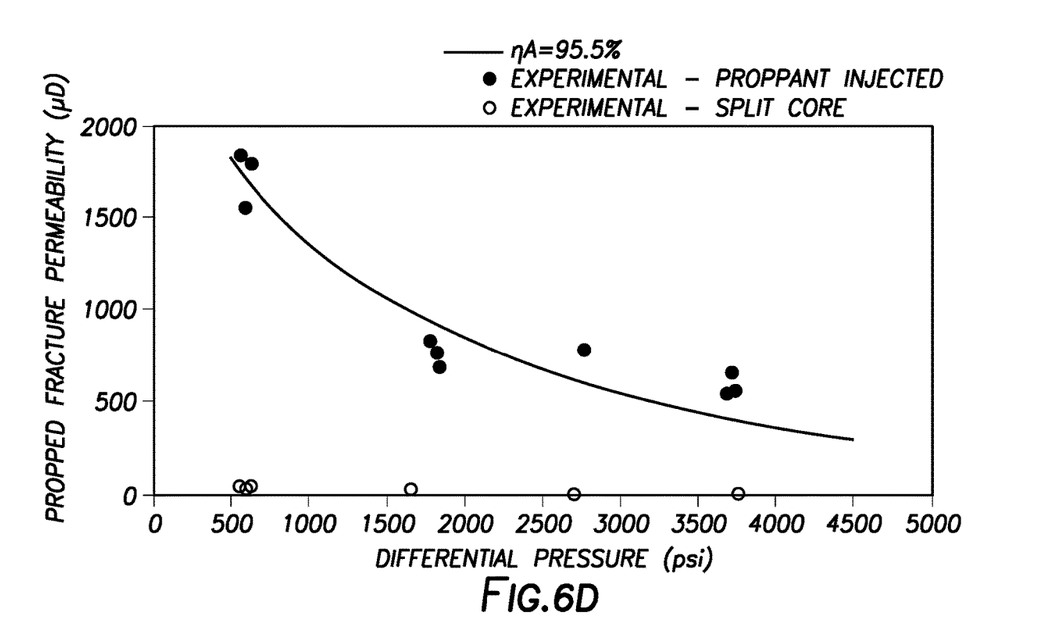

The measured permeabilities of each split core plug before and after treatment are plotted in FIGS. 6A (Bakken shale), 6B (Eagle Ford shale) 6C (Barnett shale), and 6D (Barnett outcrop). These data were analyzed using a graphical (straight-line) approach based on the proposed the fracture permeability models discussed above. After the experimental parameters of $k_0$, $p_{seal}$, and m from the unstimulated sample data and κ, Π, and M from the stimulated sample data are obtained, the proppant areal distribution factor, $\eta_A$, is determined by curve-fitting the stimulated sample data using the sum of square errors method. The results of the analysis showing the experimental and matched parameters (at the lowest least square error value of $\eta_A$) for each shale sample i shown in Tables 1-4 below.

TABLE 1

Experimental and matched parameters of Bakken shale sample

| | | After Microproppant | | |
|---|---|---|---|---|
| | Before Microproppant | | | History-matched: |
| Parameter | Experimental | Parameter | Experimental | $\eta_A$ = 11.6% |
| $k_0$ | 1,895 μD | K | 2,286 μD | 2,313 μD |
| $p_{Seal}$ | 6,038 psi | Π | 6,588 psi | 6,191 psi |
| m | 0.99 | M | 0.93 | 0.95 |

TABLE 2

Experimental and matched parameters of Eagle Ford shale sample

| | | After Microproppant | | |
|---|---|---|---|---|
| | Before Microproppant | | | History-matched: |
| Parameter | Experimental | Parameter | Experimental | $\eta_A$ = 8.9% |
| $k_0$ | 608 μD | κ | 731 μD | 792 μD |
| $p_{Seal}$ | 4,253 psi | Π | 4,996 psi | 4,488 psi |
| m | 0.90 | M | 0.89 | 0.87 |

TABLE 3

Experimental and matched parameters of Barnett shale sample

| | | After Microproppant | | |
|---|---|---|---|---|
| | Before Microproppant | | | History-matched: |
| Parameter | Experimental | Parameter | Experimental | $\eta_A$ = 24.5% |
| $k_0$ | 1,226 μD | κ | 1,962 μD | 2,020 μD |
| $p_{Seal}$ | 6,173 psi | Π | 8,244 psi | 6,677 psi |
| m | 0.88 | M | 0.73 | 0.81 |

TABLE 4

Experimental and matched parameters of Barnett outcrop shale sample

| | | After Microproppant (manual spread) | | |
|---|---|---|---|---|
| | Before Microproppant | | | History-matched: |
| Parameter | Experimental | Parameter | Experimental | $\eta_A$ = 95.5% |
| $k_0$ | 65 μD | κ | 2,850 μD | 3,365 μD |
| $p_{Seal}$ | 7,265 psi | Π | 17,047 psi | 14,790 psi |
| m | 0.92 | M | 0.55 | 0.50 |

These results demonstrate effect of the microproppants on the fluid transport. Bakken shale, with a 11.6% areal proppant placement quality, shows 400 μD improvement in permeability with zero differential pressure, and requires 550 psi of additional stress on the full closure of the fracture. M value remains nearly the same as the m value. Similarly, the Eagle Ford sample and the Barnett sample show improvements.

An embodiment of the present disclosure is a method comprising: placing a split core plug sample of a subterranean formation in a pressurizable chamber, the split core plug sample having a first end and a second end opposite the first end; pressurizing the pressurizable chamber to a first differential pressure; releasing pressure from an end of the pressurizable chamber corresponding to the first end of the split core plug sample; obtaining a first pressure change value corresponding to a decrease in pressure measured at an end of the pressurizable chamber corresponding to the second end of the split core plug sample; obtaining a second pressure change value corresponding to an increase in pressure measured at the end of the pressurizable chamber corresponding to the first end of the split core plug sample; and calculating a permeability of the split core plug sample at the first differential pressure using the first pressure change value and the second pressure change value.

Another embodiment of the present disclosure is a method comprising: obtaining a first set of data that comprises a first plurality of permeability values that each correspond to a positive permeability through a split core plug sample of a subterranean formation at one of a plurality of different differential pressures; obtaining a second set of data that comprises a second plurality of permeability values that each correspond to a positive permeability through the split core plug sample at each of the plurality of different differential pressures after a plurality of microproppant particles have been placed between two halves of the split core plug sample; extrapolating a baseline positive permeability of the split core plug sample at a differential pressure equal to zero ($k_0$) based on the first set of data; extrapolating a treated positive permeability of the split core plug sample at a differential pressure equal to zero (κ) based on the second set of data; calculating a closure resistance of the fracture (m) and the fracture closure pressure ($p_{seal}$) using the second set of data and $k_0$; estimating a proppant areal placement factor ($\eta_A$) by calculating $k_{model}$ at each of the plurality of different differential pressures for an initial value of $\eta_A$ using:

$$k = \kappa\left[1 - \left(\frac{p_c - \alpha p}{\Pi}\right)^M\right]^3$$

wherein $$\kappa = k_0\left(1 + \frac{0.78 d_p \eta_A}{\sqrt[3]{3\pi D k_0}}\left(\frac{d_p}{\sqrt[3]{3\pi D k_0} + d_p}\right)^{3/2}\right)^3,$$

$$\Pi = \frac{p_{seal} E_p (D + d_p \eta_A)(M/m)}{E_r d_p \eta_A + E_p D}\left(1 + \frac{0.78 d_p \eta_A}{\sqrt[3]{3\pi D k_0}}\left(\frac{d_p}{\sqrt[3]{3\pi D k_0} + d_p}\right)^{3/2}\right), \text{ and}$$

$$M = m(1 - \eta_A) + \eta_A\left[m\left(\frac{\sqrt[3]{3\pi D k_0}}{\sqrt[3]{3\pi D k_0} + 0.78 d_p}\right) + \zeta\left(\frac{0.78 d_p}{\sqrt[3]{3\pi D k_0} + 0.78 d_p}\right)\right],$$

and
selecting an estimated value $\eta_A$ of that minimizes a total least squares error equal to the sum of each value of $k_{model}$ and each of the second plurality of permeability values.

Another embodiment of the present disclosure is a method comprising: obtaining a first set of data that comprises a first plurality of permeability values that each correspond to a positive permeability through a split core plug sample of a subterranean formation at one of a plurality of different differential pressures, wherein obtaining at least a portion of the first set of data comprises: placing the split core plug sample in a pressurizable chamber, the split core plug sample having a first end and a second end opposite the first end, pressurizing the pressurizable chamber to a first differential pressure, releasing pressure from an end of the pressurizable chamber corresponding to the first end of the split core plug sample, obtaining a first pressure change value corresponding to a decrease in pressure measured at an end of the pressurizable chamber corresponding to the second end of the split core plug sample, obtaining a second pressure change value corresponding to an increase in pressure measured at the end of the pressurizable chamber corresponding to the first end of the split core plug sample, and calculating a permeability of the split core plug sample at the first differential pressure using the first pressure change value and the second pressure change value; obtaining a second set of data that comprises a second plurality of permeability values that each correspond to a positive permeability through the split core plug sample at each of the plurality of different differential pressures after a plurality of microproppant particles have been placed between two halves of the split core plug sample, wherein obtaining at least a portion of the second set of data comprises: placing the split core plug sample with the plurality of microproppant particles placed between two halves of the split core plug sample in a pressurizable chamber, the split core plug sample having a first end and a second end opposite the first end, pressurizing the pressurizable chamber to a second differential pressure, releasing pressure from an end of the pressurizable chamber corresponding to the first end of the split core plug sample, obtaining a third pressure change value corresponding to a decrease in pressure measured at an end of the pressurizable chamber corresponding to the second end of the split core plug sample, obtaining a fourth pressure change value corresponding to an increase in pressure measured at the end of the pressurizable chamber corresponding to the first end of the split core plug sample, and calculating a permeability of the split core plug sample at the second differential pressure using the third pressure change value and the fourth pressure change value; extrapolating a baseline positive permeability of the split core plug sample at a differential pressure equal to zero ($k_0$) based on the first set of data; extrapolating a treated positive permeability of the split core plug sample at a differential pressure equal to zero (κ) based on the second set of data; calculating a closure resistance of the fracture (m) and the fracture closure pressure ($p_{seal}$) using the second set of data and $k_0$; estimating a proppant areal placement factor ($\eta_{7A}$) by calculating $k_{model}$ at each of the plurality of different differential pressures for an initial value of $\eta_A$ using:

$$k = \kappa\left[1 - \left(\frac{p_c - \alpha p}{\Pi}\right)^M\right]^3$$

wherein $$\kappa = k_0\left(1 + \frac{0.78 d_p \eta_A}{\sqrt[3]{3\pi D k_0}}\left(\frac{d_p}{\sqrt[3]{3\pi D k_0} + d_p}\right)^{3/2}\right)^3,$$

$$\Pi = \frac{p_{seal} E_p (D + d_p \eta_A)(M/m)}{E_r d_p \eta_A + E_p D}\left(1 + \frac{0.78 d_p \eta_A}{\sqrt[3]{3\pi D k_0}}\left(\frac{d_p}{\sqrt[3]{3\pi D k_0} + d_p}\right)^{3/2}\right), \text{ and}$$

$$M = m(1 - \eta_A) + \eta_A\left[m\left(\frac{\sqrt[3]{3\pi D k_0}}{\sqrt[3]{3\pi D k_0} + 0.78 d_p}\right) + \zeta\left(\frac{0.78 d_p}{\sqrt[3]{3\pi D k_0} + 0.78 d_p}\right)\right],$$

and
selecting an estimated value of $\eta_A$ that minimizes a total least squares error equal to the sum of each value of $k_{model}$ and each of the second plurality of permeability values.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
placing a split core plug sample of a subterranean formation in a pressurizable chamber, the split core plug sample having a first end and a second end opposite the first end;
pressurizing the pressurizable chamber to a first differential pressure;

releasing pressure from an end of the pressurizable chamber corresponding to the first end of the split core plug sample;

obtaining a first pressure change value corresponding to a decrease in pressure measured at an end of the pressurizable chamber corresponding to the second end of the split core plug sample;

obtaining a second pressure change value corresponding to an increase in pressure measured at the end of the pressurizable chamber corresponding to the first end of the split core plug sample; and calculating a permeability of the split core plug sample at the first differential pressure using the first pressure change value and the second pressure change value.

2. The method of claim 1 wherein the split core plug sample comprises two halves of a split core plug placed opposite each other.

3. The method of claim 2 wherein the split core plug sample further comprises a plurality of microproppant particles between the two halves of the split core plug.

4. The method of claim 3 wherein the plurality of microproppant particles comprise at least one material selected from the group consisting of: silica flour, glass beads, fly ash, a ceramic material, bauxite, a polymer material, a polymeric composite, mica, and any combination thereof.

5. The method of claim 3 wherein the plurality of microproppant particles are placed between the two halves of the split core plug by:

placing the split core plug and the plurality of microproppant particles in a hydraulic accumulator having an interior chamber, introducing a gas into the interior chamber of the hydraulic accumulator, reducing the volume of the interior chamber to convert at least a portion of the gas to a liquid phase, wherein the plurality of microproppant particles become suspended in the liquid phase, and allowing at least a portion of the liquid phase in which the plurality of microproppant particles are suspended to enter at least a portion of a space between the two halves of the split core plug.

6. The method of claim 5 wherein the gas comprises carbon dioxide.

7. The method of claim 5 wherein the portion of the liquid phase in which the plurality of microproppant particles are suspended penetrates at least a portion of a matrix of the split core plug.

8. The method of claim 1 wherein the split core plug is formed from a generally cylindrical core plug having a diameter of about 1 inch to about 1.5 inches and a length of about 1 inch to 2 inches.

9. The method of claim 1 further comprising:

determining one or more parameters of a treatment operation in a subterranean formation from which the core plug sample was taken using the calculated permeability of the split core plug sample at the first differential pressure; and performing at least a portion of the treatment operation in the subterranean formation using the one or more parameters.

10. The method of claim 9 wherein the treatment operation comprises a hydraulic fracturing operation in which a fracturing fluid is introduced into a portion of the subterranean formation using one or more pumps at or above a pressure sufficient to create or enhance one or more fractures in the formation.

11. The method of claim 1 wherein the first pressure change value and the second pressure change value are obtained using a pressure transducer that interfaces with a computer device.

12. A method comprising:

obtaining a first set of data that comprises a first plurality of permeability values that each correspond to a positive permeability through a split core plug sample of a subterranean formation at one of a plurality of different differential pressures;

obtaining a second set of data that comprises a second plurality of permeability values that each correspond to a positive permeability through the split core plug sample at each of the plurality of different differential pressures after a plurality of microproppant particles have been placed between two halves of the split core plug sample;

extrapolating a baseline positive permeability of the split core plug sample at a differential pressure equal to zero ($k_0$) based on the first set of data;

extrapolating a treated positive permeability of the split core plug sample at a differential pressure equal to zero ($\kappa$) based on the second set of data;

calculating a closure resistance of the fracture (m) and the fracture closure pressure ($p_{seal}$) using the second set of data and $k_0$;

estimating a proppant areal placement factor ($\eta_A$) by calculating $k_{model}$ at each of the plurality of different differential pressures for an initial value of $\eta_A$ using:

$$k = \kappa \left[1 - \left(\frac{p_c - \alpha p}{\Pi}\right)^M\right]^3$$

wherein $$\kappa = k_0 \left(1 + \frac{0.78 d_p \eta_A}{\sqrt[3]{3\pi D k_0}} \left(\frac{d_p}{\sqrt[3]{3\pi D k_0} + d_p}\right)^{3/2}\right)^3,$$

$$\Pi = \frac{p_{seal} E_p (D + d_p \eta_A)(M/m)}{E_r d_p \eta_A + E_p D} \left(1 + \frac{0.78 d_p \eta_A}{\sqrt[3]{3\pi D k_0}} \left(\frac{d_p}{\sqrt[3]{3\pi D k_0} + d_p}\right)^{3/2}\right), \text{ and}$$

$$M = m(1 - \eta_A) + \eta_A \left[m\left(\frac{\sqrt[3]{3\pi D k_0}}{\sqrt[3]{3\pi D k_0} + 0.78 d_p}\right) + \zeta\left(\frac{0.78 d_p}{\sqrt[3]{3\pi D k_0} + 0.78 d_p}\right)\right],$$

and selecting an estimated value of $\eta_A$ that minimizes a total least squares error equal to the sum of each value of $k_{model}$ and each of the second plurality of permeability values.

13. The method of claim 12 wherein the plurality of microproppant particles comprise at least one material selected from the group consisting of: silica flour, glass beads, fly ash, a ceramic material, bauxite, a polymer material, a polymeric composite, mica, and any combination thereof.

14. The method of claim 12 wherein the plurality of microproppant particles are placed between the two halves of the split core plug sample by:

placing the split core plug sample and the plurality of microproppant particles in a hydraulic accumulator having an interior chamber, introducing a gas into the interior chamber of the hydraulic accumulator, reducing the volume of the interior chamber to convert at least a portion of the gas to a liquid phase, wherein the plurality of microproppant particles become suspended in the liquid phase, and allowing at least a portion of the liquid phase in which the plurality of microproppant particles are suspended to enter at least a portion of a space between the two halves of the split core plug.

15. The method of claim 14 wherein the gas comprises carbon dioxide.

16. The method of claim 14 wherein the portion of the liquid phase in which the plurality of microproppant particles are suspended penetrates at least a portion of a matrix of the split core plug sample.

17. A method comprising:
obtaining a first set of data that comprises a first plurality of permeability values that each correspond to a positive permeability through a split core plug sample of a subterranean formation at one of a plurality of different differential pressures, wherein obtaining at least a portion of the first set of data comprises:
  placing the split core plug sample in a pressurizable chamber, the split core plug sample having a first end and a second end opposite the first end,
  pressurizing the pressurizable chamber to a first differential pressure,
  releasing pressure from an end of the pressurizable chamber corresponding to the first end of the split core plug sample,
  obtaining a first pressure change value corresponding to a decrease in pressure measured at an end of the pressurizable chamber corresponding to the second end of the split core plug sample,
  obtaining a second pressure change value corresponding to an increase in pressure measured at the end of the pressurizable chamber corresponding to the first end of the split core plug sample, and
  calculating a permeability of the split core plug sample at the first differential pressure using the first pressure change value and the second pressure change value;
obtaining a second set of data that comprises a second plurality of permeability values that each correspond to a positive permeability through the split core plug sample at each of the plurality of different differential pressures after a plurality of microproppant particles have been placed between two halves of the split core plug sample, wherein obtaining at least a portion of the second set of data comprises:
  placing the split core plug sample with the plurality of microproppant particles placed between two halves of the split core plug sample in a pressurizable chamber, the split core plug sample having a first end and a second end opposite the first end,
  pressurizing the pressurizable chamber to a second differential pressure,
  releasing pressure from an end of the pressurizable chamber corresponding to the first end of the split core plug sample,
  obtaining a third pressure change value corresponding to a decrease in pressure measured at an end of the pressurizable chamber corresponding to the second end of the split core plug sample,
  obtaining a fourth pressure change value corresponding to an increase in pressure measured at the end of the pressurizable chamber corresponding to the first end of the split core plug sample, and
  calculating a permeability of the split core plug sample at the second differential pressure using the third pressure change value and the fourth pressure change value;
extrapolating a baseline positive permeability of the split core plug sample at a differential pressure equal to zero ($k_0$) based on the first set of data;
extrapolating a treated positive permeability of the split core plug sample at a differential pressure equal to zero ($\kappa$) based on the second set of data;
calculating a closure resistance of the fracture (m) and the fracture closure pressure ($p_{seal}$) using the second set of data and $k_0$;
estimating a proppant areal placement factor ($\eta_A$) by calculating $k_{model}$ at each of the plurality of different differential pressures for an initial value of $\eta_A$ using:

$$k = \kappa\left[1 - \left(\frac{p_c - \alpha p}{\Pi}\right)^M\right]^3$$

wherein $$\kappa = k_0\left(1 + \frac{0.78 d_p \eta_A}{\sqrt[3]{3\pi D k_0}}\left(\frac{d_p}{\sqrt[3]{3\pi D k_0} + d_p}\right)^{3/2}\right)^3,$$

$$\Pi = \frac{p_{seal} E_p (D + d_p \eta_A)(M/m)}{E_r d_p \eta_A + E_p D}\left(1 + \frac{0.78 d_p \eta_A}{\sqrt[3]{3\pi D k_0}}\left(\frac{d_p}{\sqrt[3]{3\pi D k_0} + d_p}\right)^{3/2}\right), \text{ and}$$

$$M = m(1 - \eta_A) + \eta_A\left[m\left(\frac{\sqrt[3]{3\pi D k_0}}{\sqrt[3]{3\pi D k_0} + 0.78 d_p}\right) + \zeta\left(\frac{0.78 d_p}{\sqrt[3]{3\pi D k_0} + 0.78 d_p}\right)\right],$$

and
selecting an estimated value of $\eta_A$ that minimizes a total least squares error equal to the sum of each value of $k_{model}$ and each of the second plurality of permeability values.

18. The method of claim 17 wherein the plurality of microproppant particles are placed between the two halves of the split core plug sample by:
  placing the split core plug sample and the plurality of microproppant particles in a hydraulic accumulator having an interior chamber,
  introducing a gas into the interior chamber of the hydraulic accumulator,
  reducing the volume of the interior chamber to convert at least a portion of the gas to a liquid phase, wherein the plurality of microproppant particles become suspended in the liquid phase, and
  allowing at least a portion of the liquid phase in which the plurality of microproppant particles are suspended to enter at least a portion of a space between the two halves of the split core plug.

19. The method of claim 18 wherein the gas comprises carbon dioxide.

20. The method of claim 17 wherein the first pressure change value, the second pressure change value, the third pressure change value and the fourth pressure change value are obtained using a pressure transducer that interfaces with a computer device.

* * * * *